United States Patent [19]

Funk et al.

[11] 4,182,183
[45] Jan. 8, 1980

[54] THERMISTOR CIRCUIT

[75] Inventors: Gerhard Funk, Meckenbeuren; Eberhard Weller; Hans-Dietrich Renovanz, both of Biberach an der Riss; Uwe Papendick, Ummendorf, all of Fed Rep. of Germany

[73] Assignee: Boehringer Ingelheim GmbH, Ingelheim am Rhein, Fed. Rep. of Germany

[21] Appl. No.: 910,067

[22] Filed: May 26, 1978

[30] Foreign Application Priority Data

May 31, 1977 [DE] Fed. Rep. of Germany ....... 2724558

[51] Int. Cl.² .............................................. G01K 7/24
[52] U.S. Cl. ................................. 73/362 AR; 219/499
[58] Field of Search .................. 73/362 AR; 219/499; 128/303.14; 83/171

[56] References Cited

U.S. PATENT DOCUMENTS 4,089,336   5/1978   Gage et al. ...................... 128/303.14

Primary Examiner—S. Clement Swisher
Attorney, Agent, or Firm—Hammond & Littell

[57] ABSTRACT

A thermistor circuit, wherein a thermistor, a current-limiting resistor, a complementary resistor and a desired-value variable resistor are connected together in the form of a resistance bridge, where the one diagonal of the resistance bridge is linked to a comparator, and the output of the comparator is connected to a bridge feed point of the other diagonal of the resistance bridge via an RC element consisting of a resistor and a capacitor and via a switching transistor.

4 Claims, 1 Drawing Figure

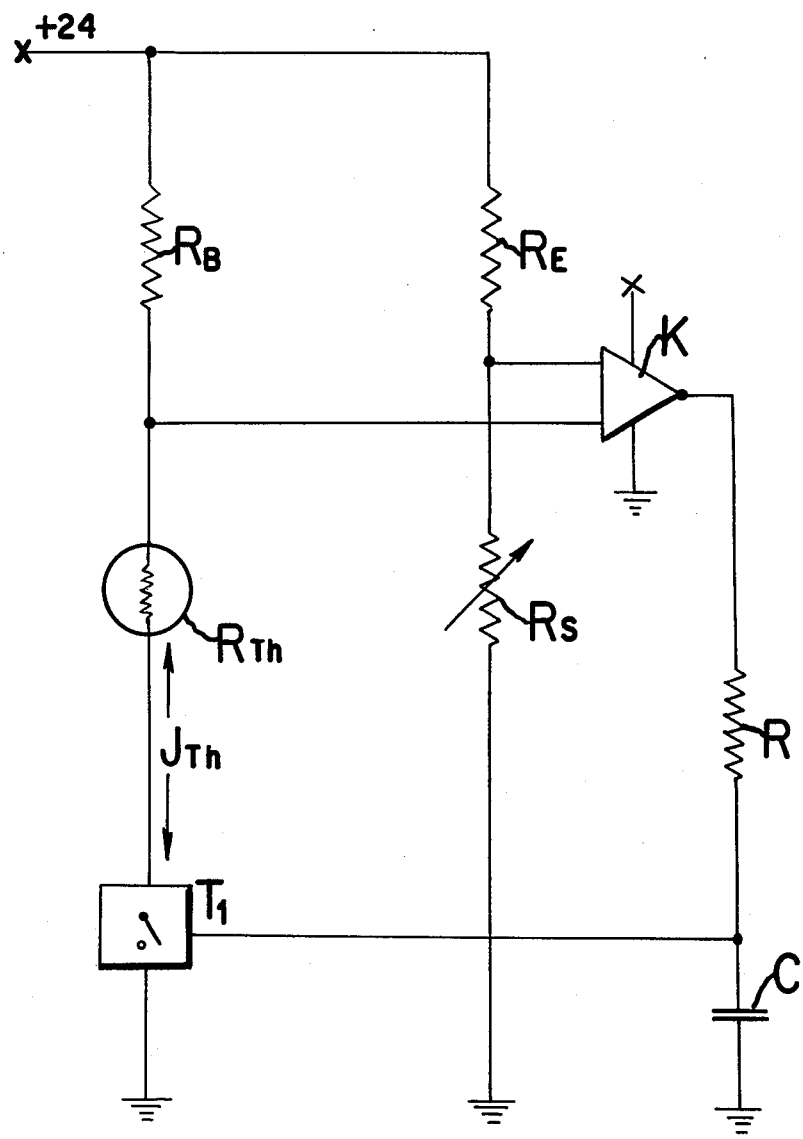

THERMISTOR CIRCUIT

This invention relates to a special circuit for a thermistor, and to the use of a thermistor equipped with such a circuit in surgery, especially in eye surgery.

BACKGROUND OF THE INVENTION AND THE PRIOR ART

Surgical cutting elements consisting of a specially formed thermistor as the core of the element are already known. These cutting instruments, which simultaneously serve as thermal sensors and as heating elements, are linked to a bridge connection (see German Offenlegungsschrift No. 2,423,537). The bridge is operated by an alternating current voltage of at least 24 Vrms. The circuit works as follows: a change in the operating temperature on the cutting instrument brings about a variation in the bridge. This causes the control signal in the diagonals of the bridge to be either in phase or out of phase with the alternating current voltage supplied. With this control signal the power is varied via a thyristor circuit, depending on the state of the bridge. The instrument is consequently able to deliver relatively quickly in a short time the heat given off. This known circuit has, however, two substantial disadvantages which do not permit such a circuit to be used universally, especially for precisely working surgical instruments: According to current regulations, medical instruments which come in direct contact with the body of the patient may not be operated at a voltage which is higher than 24 V. On the known device the rms voltage (Vrms) is 24 V. The peak voltage is obtained at 67.68 V. A lowering of this alternating-current voltage to the permissible voltage of 8.5 Vrms corresponding to 24 V peak-to-peak would mean that it would no longer be possible to furnish the required power for the cutting instrument. With the above-described type of circuit it is not possible to construct an appliance meeting the safety requirements for medical instruments.

Under the above-mentioned conditions, and especially also in view of the large passive thermal resistances of the cutting instrument, the readjustment time would become far too long at the reduced power. The effect intended with the circuit of maximal thermal constancy and rapid furnishing of heat would no longer be possible. This cutting instrument can therefore be operated only under conditions which no longer meet the safety regulations for medical instruments.

DESCRIPTION OF THE INVENTION

According to the present invention, these disadvantages, namely, operation at an already dangerous alternating-current voltage and too long readjustment times, are overcome by the circuit shown in the attached drawing, wherein a thermistor ($R_{Th}$), a current-limiting resistor ($R_B$), a complementary resistor ($R_E$) and a desired value variable resistor ($R_S$) are connected together in the form of a resistance bridge, where the one diagonal of the resistance bridge is linked at both ends to a comparator (K) and the output of the comparator is connected to a bridge feedpoint of the other diagonal of the resistance bridge via an RC element consisting of resistor (R) and capacitor (C) and via a switching transistor ($T_1$). For the sake of better understanding of the substance of the invention, reference is made here to the drawing, which illustrates the application of the essentially very simple circuit to the operation of a thermistor pill.

The thermistor ($R_{Th}$) (heating and measuring element) is connected to the operating voltage of a maximum of 24 V direct-current voltage via a transistor ($T_1$) designed as a switch. A current $$I = \frac{U}{R_{Th} + R_B}$$

now flows through the thermistor.

In the equation:
$R_{Th}$ = thermistor resistor,
$R_B$ = current-limiting resistor
U = voltage.

The thermistor is integrated into a bridge connection. A variation in the operating temperature causes a voltage in the diagonals of the bridge and is compared with a desired-value setter (S) by the comparator (K). The output of the comparator controls the base of the switching transistor ($T_1$) via an RC element (R = resistor, C = capacitor). As long as the desired value is not reached the "switch" ($T_1$) remains closed, that is, current flows through the thermistor and heats it. When the desired value is reached, the transistor ($T_1$) switches off the current $I_{Th}$. By this switch-off of the transistor the actual value on the comparator goes to zero and the transistor switches on again. This operation is, however, delayed by the capacitor (C) so that an oscillatory action occurs. The frequency of oscillations is the higher, the nearer the actual value is to the desired value. The advantage of this circuit resides in that upon slight cooling of the thermistor the supply of energy is likewise kept small and thus no overshooting of the desired temperature takes place. Upon sharp cooling, energy is supplied to the same degree, so that readjustment is made very quickly. If a very strong surge of heat occurs on the thermistor, the capacitor (C) is fully charged. When the desired value is reached the comparator switches off, but due to the existing charge of the capacitor (C) the "switch" ($T_1$) is kept closed for a period longer by the corresponding time. This last case only arises when a relatively high surge of heat has occurred beforehand. The rated value is then exceeded by a definite amount which is necessary to compensate the next surge of heat to be expected. Due to the insertion of the capacitor (C) the circuit thus extrapolates the future heat requirement to be expected in view of the previous event.

From the theoretical work by E. Andrich ["PTC Thermistors as self-regulating heating elements", Philips Technische Rundschau 30 (1969/70), 192–200] it could be expected that the control powers could be attained sufficiently only in the case of masses tending towards zero. Andrich concludes that "heating within fractions of a second cannot be achieved in the entire system to be heated, since we have not yet taken into account here the thermal resistances of the thermistor and of the materials participating passively in the heating process, including their thermal capacities. Also, only limited electrical starting powers are generally available".

In the circuit according to the invention, measurements have shown, however, that the heating times lie in the millisecond range and the control times are, again, considerably shorter. It was surprising to find that a thermistor pill approximately 1 mm in diameter, which is relatively large from theoretical point of view, is readjusted in less then 500 microseconds. The constant heat conduction of a thermistor cautery is confirmed by its behavior in the coagulation of the epithelium of the eye: a uniform removal of the epithelium is achieved even in long, very fine lines, for which the cautery has to be moved. This is brought about by the large available power of $P = U^2 R_{Th}/(R_{Th}+R_B)^2$, especially in relation to the absolute volume of the thermistor pill. A maximum of 24 V is permissible by existing safety regulations. This voltage is fully utilized in the circuit according to the invention. For example $$P = 24V^2/0.2K\Omega = 2.88 W$$

The above-mentioned known surgical cutting instrument (see German Offenlegungsschrift No. 2,423,537) can, however, subject to this maximal voltage of 24 V, furnish for example only the following power:

$$P = 8.5V^2/0.2K\Omega = 0.361 W$$

With a power of 0.361 W the known cutting instrument is no longer sufficiently controllable.

The safety of the thermistor cautery according to the invention is increased further by the fact that the extremely simple circuit has a higher operating reliability. The known circuit is no longer allowed to be used on patients with heart pacemakers, in accordance with future regulations. With the circuit according to the invention there are, however, no restrictions.

The above remarks indicate that a thermistor equipped with such a circuit is outstandingly suitable as a separating element for carrying out surgical operations, where the thermistor mass, which is spherical or designed as a cutting face, can even be relatively large; for example, the diameter of a thermistor pill can amount to several millimeters. In eye surgery the thermistor is eminently suitable as a cautery for coagulating the epithelium of the eye and for the removal thereof, for instance in the removal of dendrites of simple herpes of the cornea.

While the present invention has been illustrated with the aid of a certain specific embodiment thereof, it will be readily apparent to others skilled in the art that the invention is not limited to this particular embodiment, and that various changes and modifications may be made without departing from the spirit of the invention or the scope of the appended claims.

We claim:

1. A thermistor circuit, wherein a thermistor, a current-limiting resistor, a complementary resistor and a desired-value variable resistor are connected together in the form of a resistance bridge, where one diagonal of the resistance bridge is linked to a comparator, and the output of the comparator is connected to a bridge feed point of the other diagonal of the resistance bridge via an RC element consisting of a resistor and capacitor and via a switching transistor.

2. In a surgical cutting or coagulating instrument containing a thermistor as the cutting or coagulating element, the improvement which resides in that the thermistor comprises the circuitry of claim 1.

3. A thermistor circuit for a surgical cutting and/or coagulating instrument in the form of a Wheatstone bridge connected to a DC supply voltage, in which one diagonal is linked to a comparator and in which, when the desired value is reached for the first time, a controlled switch switches on the heating current intermittently, characterized in that the output of the comparator is connected through a resistor to the control input of said controlled switch; in that a capacitor is connected in parallel with said control input of said switch; and in that one half of said bridge is constantly connected to the bridge supply voltage source and the other half of said bridge is intermittently connected to said supply voltage through said switch.

4. A temperature control circuit for a surgical instrument including a thermistor pill whose temperature is to be kept constant while in contact with tissue being cut, comprising:
   (a) a source of DC power;
   (b) a bridge circuit containing, in one of its arms, said thermistor pill and an electronic switching element connected in series; said bridge circuit containing resistor means in its remaining arms;
   (c) comparator means;
   (d) one diagonal of said bridge circuit being connected to form the input of said comparator means, and the other diagonal of said bridge circuit being connected to said DC power source;
   (e) resistive and capacitive means connected in series between the output of said comparator and one side of said DC power source;
   (f) the junction between said resistive and capacitive means being connected to the control input of said switching means.

* * * * *